United States Patent [19]

Santoni

[11] 4,354,836
[45] Oct. 19, 1982

[54] ARTICULATOR DEVICES FOR REPRODUCING THE MOVEMENTS OF THE MANDIBLE

[76] Inventor: Pierre J. Santoni, 1, Avenue Jean Jaures, 13700 Marignane, France

[21] Appl. No.: 201,414
[22] PCT Filed: Feb. 25, 1980
[86] PCT No.: PCT/FR80/00029
   § 371 Date: Oct. 26, 1980
   § 102(e) Date: Oct. 23, 1980
[87] PCT Pub. No.: WO80/01753
   PCT Pub. Date: Sep. 4, 1980

[30] Foreign Application Priority Data
Feb. 26, 1979 [FR] France .................. 79 05426

[51] Int. Cl.³ .................................. A61C 19/04
[52] U.S. Cl. .................................. 433/73; 433/54
[58] Field of Search ............... 433/27, 54, 55, 68, 433/69, 73

[56] References Cited
U.S. PATENT DOCUMENTS
4,014,097 3/1977 Pameijer .................. 433/27

FOREIGN PATENT DOCUMENTS
1447240 6/1965 France .................. 433/68
2326906 5/1977 France .................. 433/68

Primary Examiner—Robert Peshock

[57] ABSTRACT

The invention relates to articulator devices for reproducing the movements of the mandible.

The device according to the invention comprises means for sampling the movements of the mandible, composed of an upper plate, fixed to the patient's skull and a lower plate which is fixed to the mandible by way of a buccal fork. Six displacement sensors connect the two plates together, said sensors being joined to the said plates by way of swivel joints. The device further comprises an articulator composed of two plates on which are secured the casts of the upper and lower jaws of the patient, which plates are joined together by way of artificial muscles occupying the same position as that occupied by the sensors and each muscle comprising a servomotor controlled by a sensor.

The invention finds an application in the remote- or delayed-testing and adjusting of dental prostheses.

11 Claims, 9 Drawing Figures

ARTICULATOR DEVICES FOR REPRODUCING THE MOVEMENTS OF THE MANDIBLE

The present invention relates to articulator devices for reproducing the movements of the mandible.

The technical field of the invention is that of dental instruments and prostheses.

Apparatuses, known as articulators, exist which permit to reproduce mechanically certain movements of the mandible. Said articulators comprise two supports hingedly connected together, on which are fixed casts of the upper and lower jaws. They are designed to test and adjust dental prostheses, without the patient being present.

Amongst these articulators, we find the non-adaptable articulators based on average anatomical dimensions and the adaptable articulators permitting to alter the course of the movements from recordings made on the patient's mouth. We know, for example, the articulators of Gysi, of Hanau, the Dentatus articulator, the Gerber articulator, etc . . . Such articulators are described for example in French Pat. No. 1 447 240 and in British Pat. No. 4 014 097. The first relates to a device which comprises a measuring apparatus for recording the mastication movements three-dimensionally, and an articulator provided with two reproducing members, movable with respect to one another, to sharpen the masticatory surfaces of the artificial teeth. The second relates to a method and device for measuring and recording the mastication movements three-dimensionally, and mechanically or electrically, wherein the movements of the different reference elements, arranged in relation to the upper and lower jaws, are recorded.

All these mechanical articulators are imperfect. Indeed, temporo-mandibular articulations are complex and not very well known articulations which permit not only the opening and closing movements but also the protrusion and laterality movements of one jaw with respect to the other. These articulations are mechanically difficult to make and they do not accurately reproduce the natural articulations.

It is one object of the present invention to propose articulators which have no articulation between the two plates carrying the casts of the jaws, and thus to facilitate the production of these articulations and the access to the casts of the jaws from the back.

An odontograph, such as described in French Pat. No. 2 326 906, has been proposed to palliate to any inadequacies of reproduction of prostheses, which odontograph is designed to be associated to existing mechanical articulators. The same disadvantage is found with this apparatus as with the other mechanical articulators, namely that it is very difficult to mechanically record the movements of the mandible for remote and/or delayed reproduction. Moreover, the mechanical recording makes it possible to graphically record the movements of one or more points in one or more planes, but it is very difficult afterwards to recreate, from these graphical recordings, the real movement of the mandible.

Another object of the present invention is to propose devices which make it possible to remotely reproduce or to record for delayed reproduction and to repeat the usual movements of the mandible with great accuracy, as far as the displacements of each point and the dynamics of such displacements as well as the positions are concerned.

A device according to the invention is of the articulator type, and comprises, in known manner, two supports movable one with respect to the other, on which are respectively fixed casts of the upper and lower jaws of a patient and means for actuating the said supports in order to recreate the movements of the mandible of the patient.

The objects of the present invention are attained with a device comprising:

on the one hand, means for sampling the movements of the mandible consisting of a plurality of sensors of linear displacement which are fixed by their ends to the patient's skull and mandible respectively, and which convert analogically the linear displacements into electrical signals;

on the other hand, an articulator composed of two plates on which are fixed the said casts of the upper and lower jaws, said plates being joined together by artificial muscles only, the said artificial muscles occupying positions identical to the positions of said sensors, and each comprising a linear servomotor;

and electronic circuits binding each servomotor to the corresponding sensor.

According to one preferred embodiment of the invention, the electronic circuits are provided with means for recording the electric signals issued by the said sensors and with means for reading the recorded signals and for their delayed transmission to the binding circuits of the said servo-motors.

The movement-sampling means advantageously comprise an upper plate fixed to the patient's skull and mandible respectively and connected together by at least six displacement sensors, each sensor being composed of two aligned rods, slidable one with respect to the other, and the ends of which are connected by way of swivel joints, to the upper plate and to the lower plate respectively, and of a transducer which sends an electric signal proportional to the translational displacement of one rod in relation to the other.

According to a preferred embodiment of the present invention, the displacement sensors are composed of two tubes sliding telescopically one into the other, one tube carrying a source of light such as for example an electroluminescent diode, and the other a photosensitive detector, such as for example a photoresistor.

The articulator proper comprises:

a fixed support, formed by gantries for example;

an upper plate fixed to said support, and on which is fixed the cast of the upper jaw;

and a lower plate, on which is fixed the cast of the lower jaw, said lower plate being suspended on said upper plate by way of at least six artificial muscles, each muscle comprising two aligned rods sliding axially one with respect to the other, and connected by means of swivel joints to the said upper plate and to the said lower plate respectively, and a linear servomotor which comprises two tabs, reversedly movable in translation one with respect to the other, said tabs being fixed respectively to the two rods and the said servomotor being controlled by the signal sent by the sensor to which it corresponds.

The result of the invention is a new electronic articulator which makes it possible to reproduce in real time or with a delay, on the spot or remotely, all the natural movements of a patient's mandible with great space and dynamic fidelity.

The invention also relates, on the one hand, to the movement sampling and recording device used by the dentist, and on the other hand, to the articulator device proper which is used by dental technicians and mechanics to reproduce the recorded movements and to test and adjust all types of dental prosthesis, for example permanent prostheses such as crowns or bridges, removable prostheses or total prostheses. The articulator permits the carving of the occluding faces of the artificial teeth of prostheses so that their shape can adapt to all the natural movements of the jaws.

A device according to the invention is particularly advantageous whenever the adjustment of a prosthesis raises delicate problems of equilibrium.

A device according to the invention makes it possible to reproduce and recreate accurately, without the patient being present, all the mastication and phonation movements of the mandible and to simulate exactly the dynamic movement of prostheses.

One advantage of the devices according to the invention is that they can easily be produced from a small number of electronic components which are standard and inexpensive so that they cost less to produce than any of the known mechanical articulators.

Another advantage of the devices according to the invention resides in the fact that the movement sampling device is composed of lightweight sensors which slide without any friction one with respect to the other and do not impair the natural movements of the patient.

Another advantage of the devices according to the invention resides in the fact that all the information required to produce the movement of the mandible is given in the form of electrical signals. Said electrical signals can be remotely transmitted instantly, thereby allowing a telereproduction of the movement to be made in real time. The electrical signal can also be recorded in analog or digital form, on standard recorders, such as for example magnetic tapes, this permitting to obtain an inexpensive recording.

A major advantage of the devices according to the invention over the known mechanical articulators is that the two plates are no longer hingedly connected, this avoiding the necessity to produce two complex temporo-mandibular articulations.

The invention will be more readily understood on reading the following description with reference to the accompanying drawings, in which.

Figure 1:
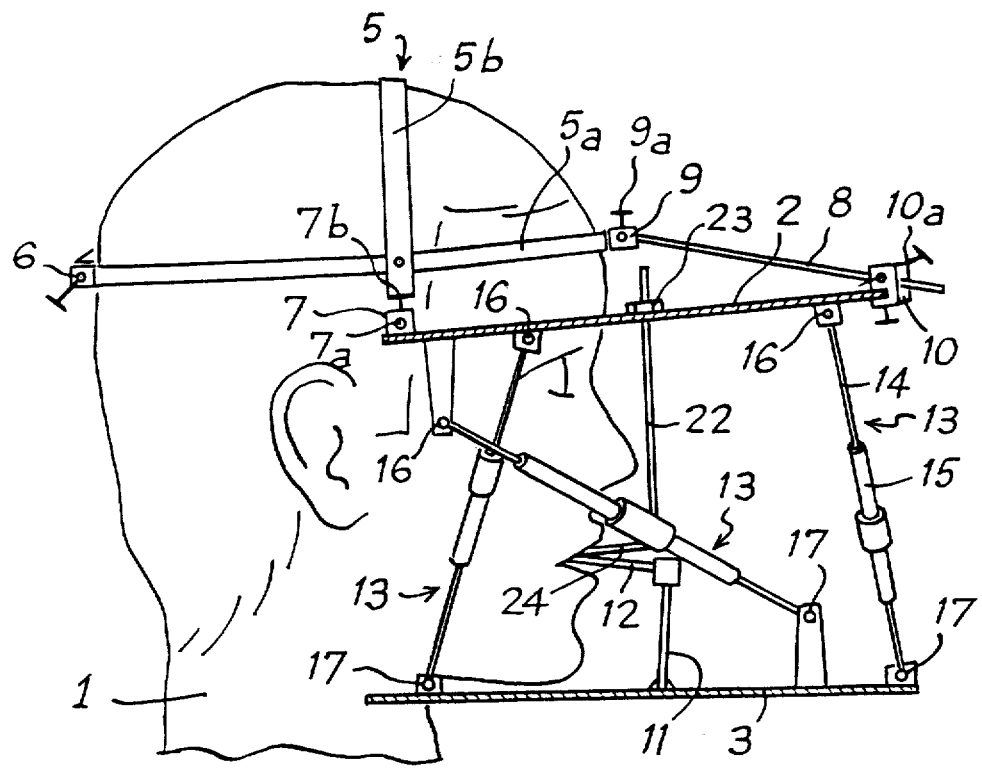
FIG. 1 is an overall view of the movement sampling device.
Figure 3:
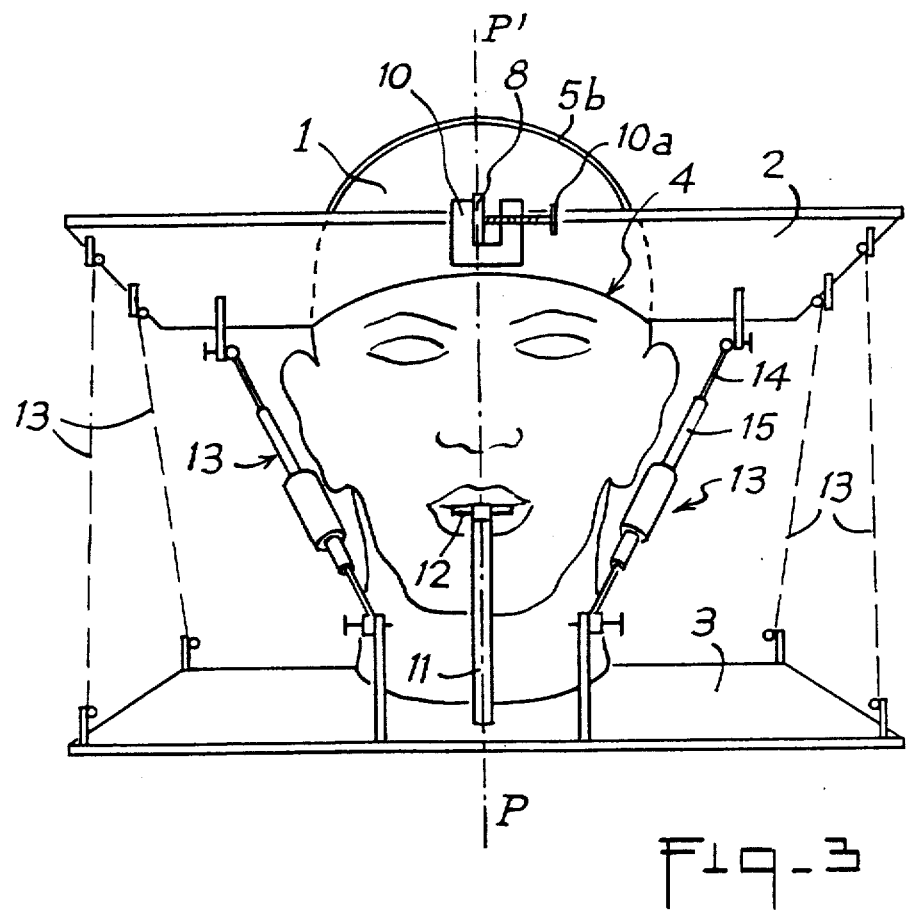
FIG. 3 is a front view of the device shown in FIG. 1.

FIGS. 1 and 3 show a device for sampling the movements of the mandible, fitted on a patient's head 1. Said device comprises an upper plate 2 which is fixed to the patient's skull and a plate 3 which is integral with the patient's mandible. The word plate is used in the generic sense to designate any rigid support of any shape whatsoever. The plate 2 is vizor-shaped with a cut-out part 4 to receive the patient's forehead. The plate 2 is fixed to a helmet 5 which covers the skull. Said helmet 5 comprises for example a horizontal belt or hoop 5a which encircles the skull and is provided at the back with a gripping device 6 of any known type, for example a screwing device. The helmet 5 further comprises a second belt or hoop 5b situated in a frontal plane. The helmet 5 can of course be produced differently.

The plate 2 comprises two fastening members 7 which are joined to the ends of the hoop 5b by means of a joint 7a. A screw 7b permits to lock these joints in a predetermined position. The plate 2 is connected to the helmet 5 by a rod 8. The hoop 5a supports at the front two extensions forming a fork 9 in which is pivotally mounted one end of the rod 8. A screw 9a locks this joint in position. The other end of the rod 8 slides between two flanges 10 provided on the plate 2. A screw 10a permits to lock the rod 8 in position between the flanges and to vary the length of the rod 8. It is understandable that, by playing on the joints 7a and on the length of the rod 8, it is possible to control the position of the plate 2 with respect to the helmet and then to lock the plate 2 in a position where it is fast with the helmet and with the patient's skull.

Other, equivalent, means can of course be used to secure the plate 2 or any other equivalent support, to the patient's skull.

The plate 3 is joined to the mandible by a rod 11 which carries an intra-buccal metal fork 12 which rests against the external face of the teeth of the lower jaw.

Said fork 12 is coated with a hard-setting paste, such as an instant-setting polymerizable resin, and is fixed to the teeth with a few drops of adhesive, such as for example a cyanoacrylate adhesive. Any other equivalent means can of course be used to fix the fork 12 on the lower jaw. The rod 11 and fork 12 assembly causes the plate 3 to move as one piece with the mandible in all directions.

The plates 2 and 3 are joined together by six displacement sensors 13 which are symmetrical in pairs with respect to the sagittal plane PP'. For clearness purposes, said sensors have been shown in the drawings by a broken line. The three sensors situated on the same side of the plane PP' are arranged in three directions which are not parallel in pairs, so that they define three axes and that any movement of the plate 3 with respect to the plate 2 can be decomposed into three movements directed according to said three axes.

Figure 2:
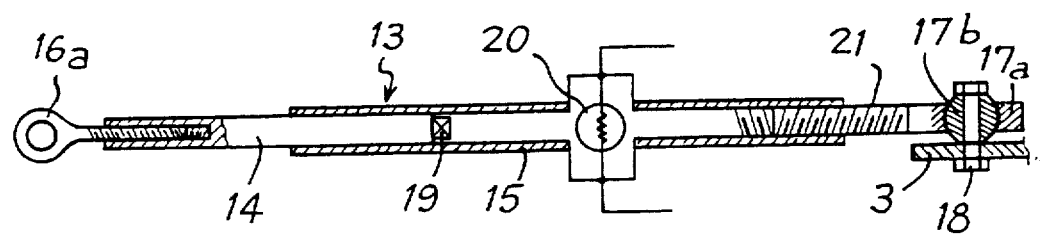
FIG. 2 is an axial cross-section of an embodiment of a displacement sensor.

FIG. 2 shows, on an enlarged scale, one of the sensors 12 which are all composed in the same way. Each sensor 13 consists of two aligned rods 14 and 15 sliding freely with respect to one another, for example two tubes sliding in telescopic manner one inside the other. The two ends of the two rods are joined, via swivel joints 16 and 17, to the upper plate and to the lower plate respectively. For example, the two free ends of the rods 14 and 15 comprise a circular eyelet 16a, 17a which engages a small spherical barrel, such as small barrel 17b which is secured via a bolt 18 to the plate 3. Said eyelets and barrels can of course be replaced by swivel joints, pivoting in any direction in spherical cavities provided on the plates 2 and 3. Such swivel joints allow the sensors 13 to move freely in all directions with respect to the plates 2 and 3.

In the embodiment illustrated in FIG. 2, the tube 14 is provided at its end with an electroluminescent diode 19 which is fed with a low voltage electrical current of 2.5 volts for example, to avoid all risks of electrocution. The tube 15 contains a photoresistor 20 which receives the light emitted by the diode 19 and whose resistance varies as a function of the amount of light it receives, hence in relation to the distance at which the diode is placed. The resistance of the photoresistor decreases when the diode moves away but the law of variation is not linear. An electronic device described hereinafter makes it possible to restore the linearity. The assembly composed of the photoelectric resistor and of the electronic device constitutes a transducer which converts analogically the movement of the tube 14 with respect to the tube 15 into a proportional electrical signal. Such transducer can of course be replaced by any other equivalent linear displacement transducer, such as for example a linear potentiometer.

The embodiment illustrated in FIG. 2 with a photoelectric transducer is preferred since it entails no friction of one tube on the other and since the sensors have a very low inertia and do not impair the natural movements of the mandible. The diode 19 can of course be replaced by any other source of light and the photoresistor 20 by any other photoelectric detector.

The sensors 13 further comprise a threaded pin 21 which is screwed in a tapped hole provided in the tube 15 and which makes it possible to adjust the length of the sensor in the rest position in relation to the distance separating the plates 2 and 3. Preferably, the end parts of the sensors where the eyelets 16a and 17a are situated are in plastic material so as to electrically isolate the sensors from the plates 2 and 3.

There is shown in FIG. 1 a threaded pin 22 whose top end is screwed in a nut 23 secured to the plate 2, this permitting to vary the length of the pin 22 situated beneath the plate. Said pin 22 is provided at its lower end with a buccal fork 24 which is introduced inside the mouth of the patient, where it rests on the occluding face of the upper jaw, via a ball of hard-setting paste which is molded onto the teeth. Said fork is used to transfer onto the articulator proper the distance separating the upper plate from the occluding face of the teeth of the upper jaw.

Figure 4:
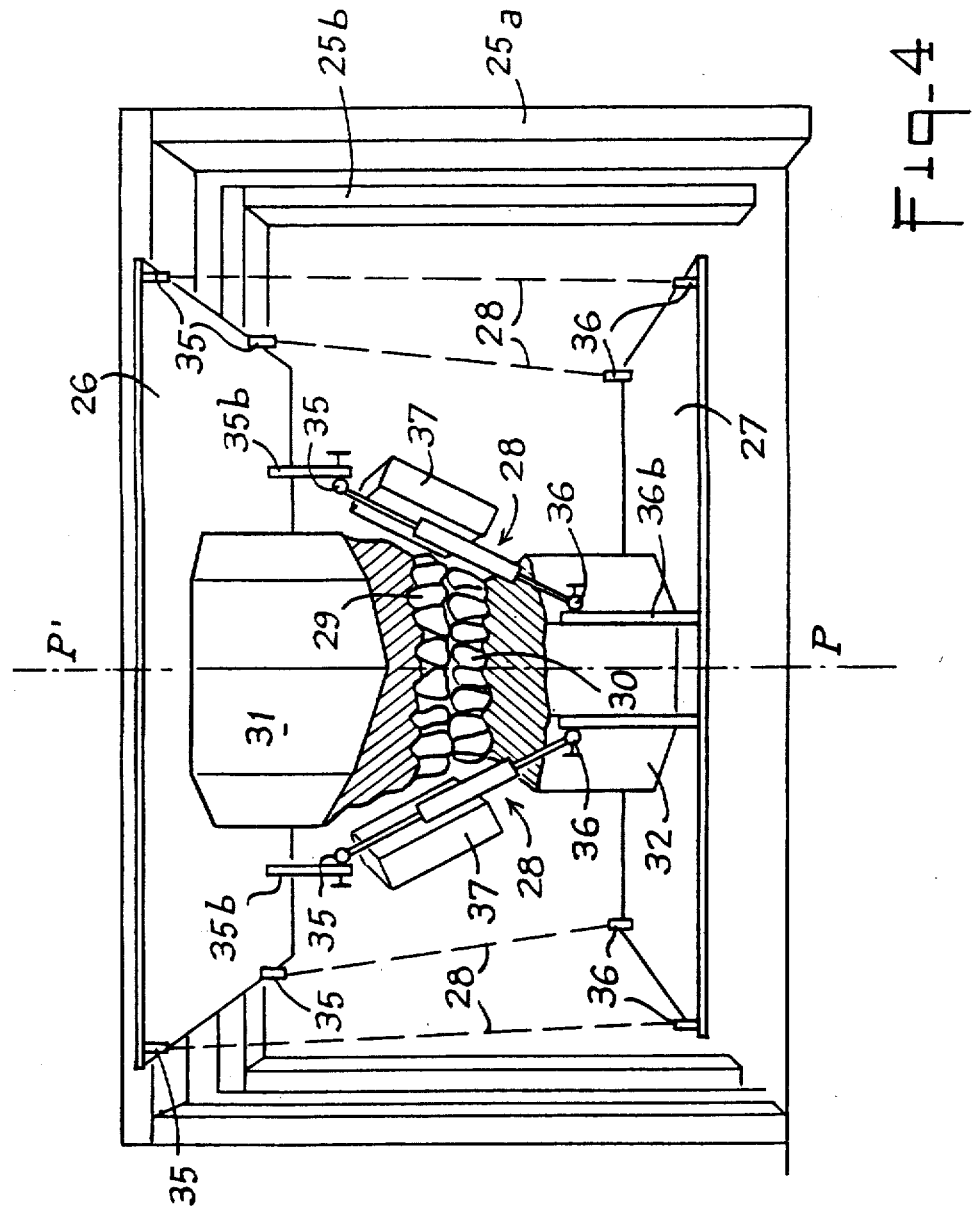
FIGS. 4 and 5 are respective side and front views of the articulator proper in a device according to the invention.
Figure 5:
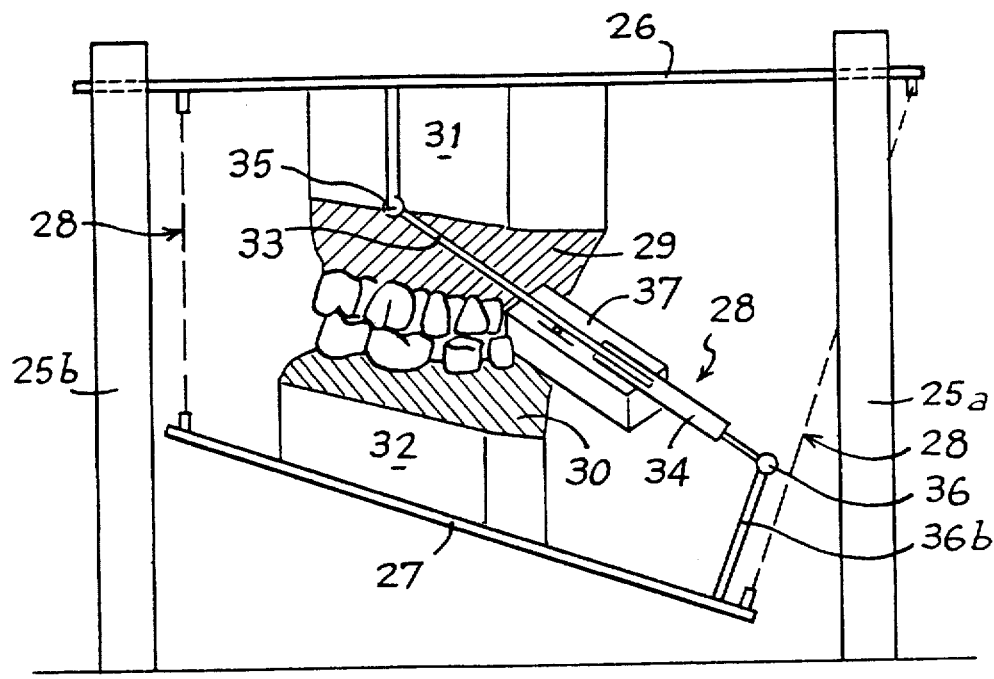

FIGS. 4 and 5 illustrate an embodiment of the articulator proper of a device according to the invention. Said articulator comprises a fixed support, having for example the shape of two gantries 25a and 25b, on which is fixed an upper plate 26. It further comprises a lower plate 27 which is suspended to the plate 26 by way of six artificial muscles 28. The six muscles 28 are identical in structure and for clearness purposes these have been shown in the drawings as dotted lines. On the plates 26 and 27 are fixed respectively a cast 29 of the upper jaw and a cast 30 of the lower jaw of the patient. Said casts 29 are 30 are secured to the plates 26 and 27 by any known means, such as for example by two rigid supports 31 and 32 and blocks of hardsetting paste.

Each sensor and each artificial muscle are first placed in abutment and their lengths are equalized individually using the threaded pins. The position of the upper plate is then adjusted with respect to the patient's skull so that, when the jaws are closed, the sensors are substantially at half way. Then using the fork 22, 24, the upper jaw 29 is positioned so that the occluding faces of the teeth of the casts are separated from the upper plate 26 by a distance which is equal to the distance separating the plate 2 from the occluding faces of the teeth of the patient's upper jaw. The six artificial muscles 28 occupy, with respect to the two plates 26 and 27 and to the casts 29 and 30, relative positions which are identical to those occupied by the sensors 13 with respect to the plates 2 and 3 and with respect to the patient's jaws. In particular, the muscles 28 are symmetrical in pairs with respect to a sagittal plane PP'. It is specified that the two plates 26 and 27 are linked together by the artificial muscles 28 only and that, especially, they are not joined by any hinged connection.

Figure 6:
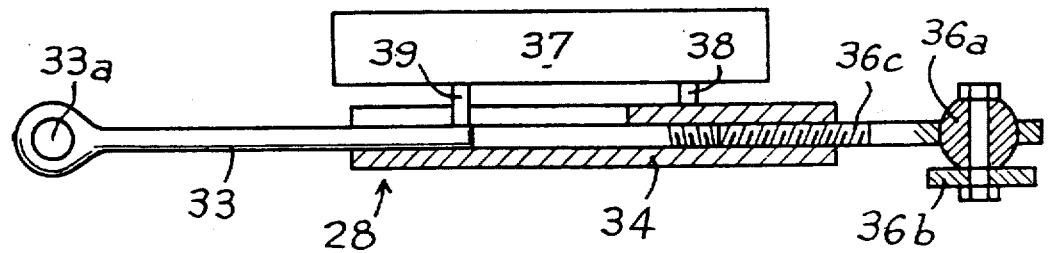
FIG. 6 is an axial cross-section of one of the artificial muscles of the articulator.

FIG. 6 shows on an enlarged scale and in axial cross-section, one of the said artificial muscles 28. Each muscle 28 comprises two aligned stems 33 and 34 capable of sliding axially with respect to one another, such as for example two tubes sliding in telescopic manner. The two ends of the muscle are connected respectively to the plates 26 and 27 by means of swivel joints 35 and 36, identical to the joints connecting the sensors 13 to the plates 2 and 3. For example the rods 33 and 34 are provided at their end with an eyelet 33a, 34a which engages a spherical barrel 35a, 36a fixed on a support 35b, 36b integral with one of the plates 26 or 27. One of the hinged connections, 36 for example, is borne by a threaded pin 36c which screws into a thread of the type of 34 and permits to adjust the total length of the muscle. Each muscle 28 further comprises a servo-motor 37 of a known type comprising for example an electric motor driving two racks in opposite directions, said racks carrying two tabs 38 and 39 which move in a straight line and in opposite directions. The tab 38 is fixed for example to the tube 36 whereas the tab 39 is fixed to the tube 33 and slides in a longitudinal slot provided in the tube 34. This type of servo-motor and the so-called floating assembly on the two tubes 33 and 34 are well known in servo-mechanisms. The floating assembly makes it possible to double the serviceable stroke of the servo-motor. Each servo-motor 37 is controlled by the signal sent by the sensor 13 to which it corresponds, so that each artificial muscle 28 reproduces accurately the elongation movements of the sensor 13 to which it corresponds and the composition of the elongation movements of all the muscles makes it so that the relative movement of the plate 27 with respect to the plate 26 reproduces accurately the relative movement of the plates 2 and 3 and, as a result, the relative movement of the casts 29 and 30 reproduces exactly all the movements of the patient's mandible.

Figure 7:
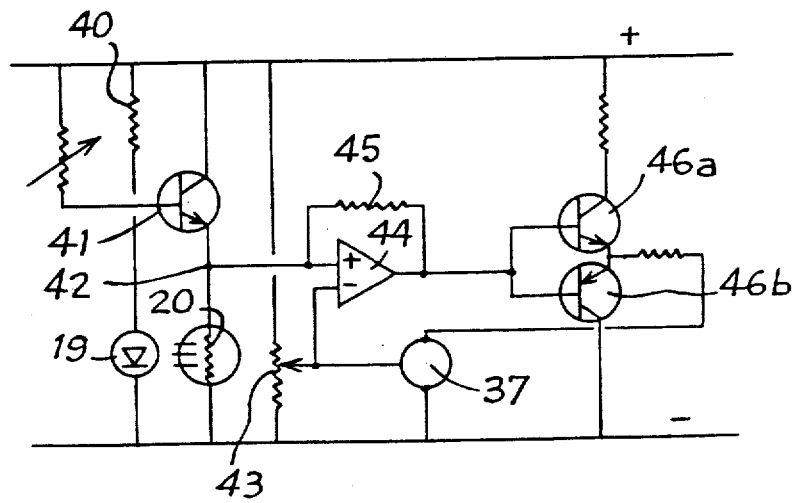
FIGS. 7, 8 and 9 are block diagrams of the main electronic circuits of a device according to the invention.

FIG. 7 is an electronic diagram illustrating the electroluminescent diode 19 and the photoresistor 20 of a sensor. The diode 19 is supplied continuously with a low voltage, about 2.5 V, via a resistor 40. The photoresistor 20 is placed in the circuit of a transistor emitter 41. The output voltage is taken at point 42 of the transistor emitter 41. It was noted that the resistance of the photoresistor 41 did vary in non-linear manner in relation to the relative movement of the rods 14 and 15. Considering that the range of variations of the resistance is important, the characteristics of the transistor 41 vary also in non-linear manner and the non-linearity of the variations of gain of the transistor substantially compensate the non-linearity of the variation of resistance. Thus the pressure obtained at point 42 varies linearly in relation to the relative linear displacement of the rods 14 and 15 of the sensor.

FIG. 7 further shows the servo-motor 37 which corresponds to the sensor and which is under its control. Said servo-motor drives the cursor of a potentiometer 43 which delivers a voltage varying in relation to the position of the servo-motor.

The control circuit essentially comprises, in known manner, an operational amplifier 44, mounted as a comparator, which compares the voltage delivered by the sensor at point 42 with the voltage delivered by the potentiometer 43. A feedback resistor 45 makes it possible to reduce the gain of the amplifier. The output of the amplifier 44 is connected to a power amplifier composed of two transistors 46a and 46b mounted in opposition (push-pull). The output of the power amplifier controls the servo-motor 37 in the direction which cancels the variation between the two voltages at the input of the comparator 44.

FIG. 7 shows an example of transmission of the movements of the mandible in real time to the articulator. It is however specified that the articulator can also be placed at a great distance from the movement device and in such a case, the voltages delivered at points 42 are easily remote-transmitted via telecommunication lines and its is thus possible to obtain a telereproduction of the movement of the mandible.

Figure 8:
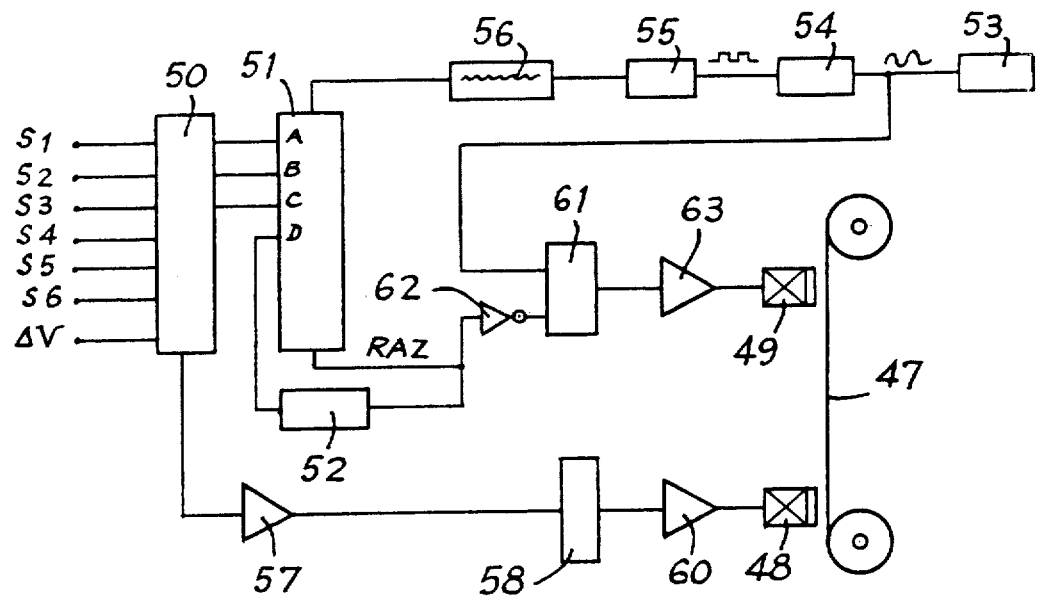

FIG. 8 is a block diagram of the main components of the circuits permitting to record the signals emitted by the sensors 13 for subsequent reading, this permitting to give a delayed reproduction of the movements of the mandible, whether on the spot or remotely, and to repeat them several times. The signals are recorded on two tracks of a tape recorder 47. The reference marks 48 and 49 represent the two recording heads corresponding to the two tracks.

Outputs S1 to S6 of the six sensors, taken at points 42 in FIG. 7, are connected to six inputs of a multiplexor 50. Said multiplexor comprises a seventh input to which is applied a constant voltage of 1 V intended for calibrating the apparatus. Said multiplexor 50 is controlled by a binary pulse counter 51 with four outputs A, B, C, D. Outputs A, B, C control the changes of input channel of the multiplexor. Output D is connected to a monostable 52 which delivers a pulse whose duration is greater than a clock period. The output of the monostable 52 is connected to the zero-setting of the counter 51.

The input of counter 51 is connected to a chain comprising a clock 53 delivering a sinusoidal signal, a circuit 54 for shaping the clock signals which delivers rectangular pulses, a circuit 55 which is meant to render the signals compatible with T.T.L. components and a second monostable 56 which is meant to compensate the dephasing due to the shaping of the clock signals during reading.

The output of the multiplexor 50 is connected to an amplifier 57, which is an impedance adaptor. The output of the amplifier 57 is connected to a converter circuit 58 which converts analogically the voltages V into frequencies f according to a law of the form $f = fo - KV$, namely a linear law with negative conductance.

The conversion of the voltages into frequencies is necessary since it frequently happens that the voltage delivered by a sensor remains constant or varies vary slowly throughout the sampling of the movements and the tape-recorder cannot record continuous voltages. The output of the converter 58 is connected to a recording preamplifier 60 whose output is connected to the recording head 48 of the track No. 1 of the tape-recorder.

The circuits further comprise an analog multiplier unit 61 whose two inputs are connected one to the output of the clock 53 and the other to the output of the monostable 52 via an inverter 62. A sinusoidal signal is obtained at the output of the circuit 61 which signal is interrupted throughout the duration of the clearing pulses delivered by the monostable 52. This signal is recorded on track No. 2 of the tape-recorder after going through a pre-amplifier 63 and the recording head 49.

Figure 9:
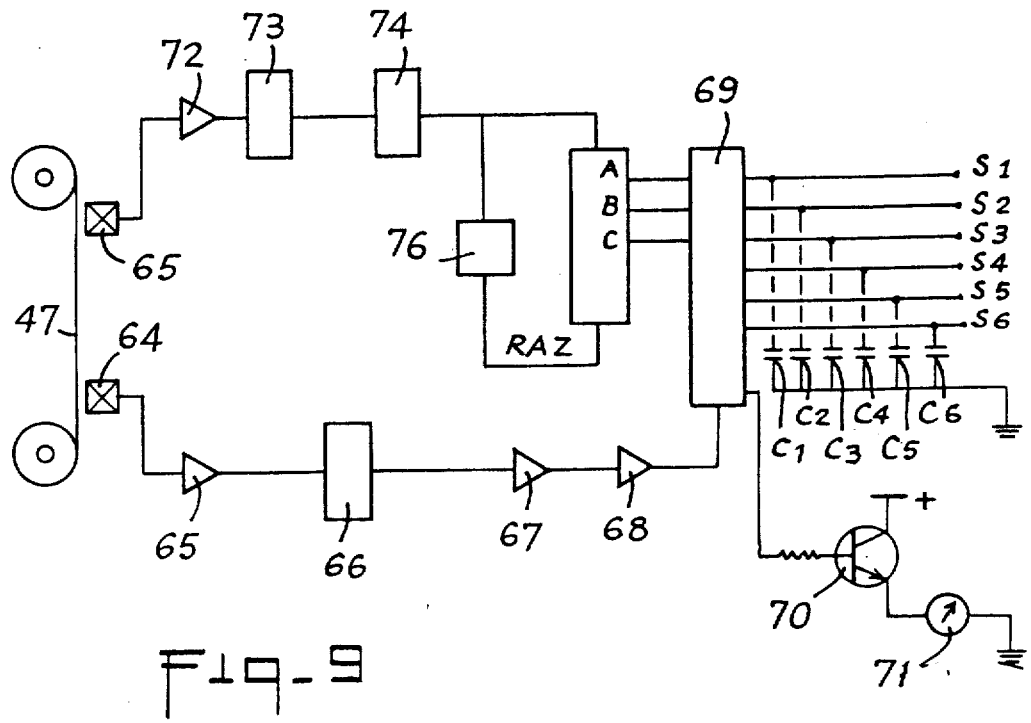

FIG. 9 is a block diagram of the reading circuits for the signals recorded on the magnetic tape of the tape-recorder 47. Reference marks 64 and 65 designate the reading heads of the tracks 1 and 2 of the tape-recorder. The signals read by the reading head 64 are amplified by a pre-amplifier 65. The output of the amplifier 65 is connected to an analog converter circuit 66, which converts the frequencies into voltages. The output of the converter 66 is connected to the input of an operational amplifier mounted as an adder with adjustable gain which is meant to reverse the variation direction of the voltage in relation to the frequency, which has been reversed by the converter 58 during recording, producing, as we have seen, a linear function with negative conductance. The output of the amplifier 67 is connected to the input of a demultiplexor 69 via an impedance adaptor amplifier 68. The demultiplexor 69 comprises seven outputs. On six of these, numbered S1 to S6, the voltage obtained corresponds to the voltage delivered at point 42 by one of the sensors. Each output S1 and S6 is connected to a control device of a servo-motor according to FIG. 1. The outputs of the multiplexor are each connected in known manner to condensers C1 to C6 which condensers constitute integrators storing the output voltage of each channel throughout one cycle of the demultiplexor.

The seventh output channel is connected via a transistor 70 on a galvanometer 71 which permits to control the level of the reference voltage. The signal read by the reading head 65 is amplified and shaped by an amplifier and then rendered compatible with the TTL circuits by way of an interface circuit CMOS-TTL 73.

The output of the interface circuit 73 is connected on the input of a pulse shaping and inverter circuit 74 which delivers clock pulses controlling a pulse counter 75 which controls the demultiplexor 69.

The output of the pulse shaping circuit 74 is connected also to an integrator 76, which extracts the zero-setting pulses from the complex signal, recorded on track 2, and send them on the zero-setting of the counter 75.

The signal-multiplexing and demultiplexing electronic circuits as well as the recording and reading circuits are well known of technicians in electronics and it is not necessary to describe them in more detail.

It is understood that the different elements constituting the electronic devices and circuits described hereinabove can be replaced by equivalent elements fulfilling the same functions, and this without departing from the invention. For example the twin-track magnetic recorders can be replaced by multi-track recorders thus permitting a simplification of the electronic circuits, particularly by eliminating the multiplexing although this has one disadvantage which is that expensive tape-recorders have to be used.

What is claimed is:
1. A dental device comprising:
means for analogically converting the movements of a patient's mandible into electric signals, comprising an upper plate and a lower plate, said plates to be fixed to the patient's skull and mandible respectively, and six sensors of linear displacement which have ends articulated respectively to said upper and lower plate;
and a dental articulator comprising two plates on which are fixed respectively a cast of the patient's upper and lower jaw, said articulator plates being connected with each other by six extensible stems, each having two ends which are articulated respectively to said two articulator plates and which six stems occupy relative positions which are respectively identical to the positions of the six sensors, each extensible stem comprising a linear servomotor;

and electronic means comprising electronic circuits connecting respectively each servomotor to a sensor so that said servomotor moves the extensible stem carrying it and reproduces accurately the elongation movements of the sensor.

2. A dental device according to claim 1, wherein said electronic means comprise means for recording the electric signals issued by said sensors, and means for reading the recorded signals and for their delayed transmission to said connecting circuits of each servomotor.

3. A dental device according to claim 1, wherein each sensor comprises two aligned rods slidable with respect to one another, an end of each rod being articulated to said upper and said lower plate respectively, and a transducer which converts analogically the translation displacement of one rod with respect to the other into a proportional electric signal.

4. A dental device comprising:
   means for analogically converting the movements of a patient's mandible into electric signals comprising an upper plate and a lower plate which are to be articulated to the patient's skull and mandible respectively, and six sensors of linear displacement which are composed of two tubes sliding telescopically one into the other, an end of each tube being articulated to said upper and said lower plate respectively and one tube carrying a source of light, and the other tube carrying a photosensitive detector which emit an electric signal proportional to the distance between said source of light and said detector;
   and a dental articulator comprising two plates on which are fixed respectively a cast of the patient's upper and lower jaw, said articulator plates being connected with each other by six extensible stems, each having two ends which are articulated respectively to said two articulator plates and which six stems occupy relative positions which are respectively identical to the positions of the six sensors, each extensible stem comprising a linear servomotor;
   and electronic means comprising electronic circuits connecting respectively each servomotor to a sensor so that said servomotor moves the extensible stem carrying it and reproduces accurately the elongation movements of the sensor.

5. A dental device according to claim 4, wherein said source of light is an electroluminescent diode and said photosensitive detector is a photoresistor.

6. The dental device according to claim 4, wherein said upper plate is visor-shaped with a cut-out part to receive the patient's forehead, said upper plate being fixed to a helmet which covers the patient's skull by means of two lateral joints and of a frontal rod of adjustable length.

7. The dental device according to claim 4, wherein said articulator comprises:
   a fixed support;
   an upper plate fixed to said support, and on which is to be fixed the cast of the upper jaw;
   and a lower plate, on which is to be fixed the cast of the lower jaw, said lower articulator plate being suspended on said upper articulator plate by way of at least six artificial muscles, each muscle comprising two aligned rods sliding axially one with respect to the other, and connected by means of swivel joints to said upper articulator plate and to said lower articulator plate respectively, and a linear servomotor which comprises two tabs, reversedly movable in translation one with respect to the other, said tabs being fixed respectively to said two rods, and said servomotor being controlled by the signal sent by the sensor to which it corresponds.

8. The dental device according to claim 4, wherein said rods constituting said displacement sensors and said artificial muscles comprise a threaded pin permitting to adjust their length.

9. The dental device according to claim 2, wherein said electronic recording circuits comprise a multiplexor whose input channels are connected to the output of said displacement sensors, a voltage-frequency converter converting analogically the voltages delivered by the multiplexor into frequencies, a clock which controls a pulse counter controlling said multiplexor, a monostable whose input is connected to the last output channel of said pulse counter and whose output is connected to the zero-setting of said pulse counter, an analog multiplier unit whose two inputs are connected, one to said clock, and the other, via an inverter, to the output of said monostable, and a two-track tape recorder on the first track of which are to be recorded the signals sent by said voltage-frequency converter, and on the second track of which are to be recorded the signals sent by the analog multiplier unit.

10. The dental device according to claim 9, wherein the electronic reading circuits used for reading the information recorded on said tape recorder comprise a converter converting the frequencies into voltages, whose input is connected to the reading head of the first track of said recorder, a demultiplexor whose input is connected to the output of said frequency-voltage converter, a pulse counter controlling said demultiplexor, a pulse-shaping and inverter circuit whose input is connected to the reading head of the second track of said recorder and whose output is connected, to the input of said pulse counter, and via an integrator circuit, to the zero-setting terminal of said pulse counter.

11. The dental device according to claim 4, wherein said support is formed by gantries.

* * * * *